United States Patent
Hughes et al.

(10) Patent No.: US 10,300,200 B2
(45) Date of Patent: May 28, 2019

(54) AUTOMATIC INJECTION DEVICE WITH NEAR-FIELD COMMUNICATION

(71) Applicant: AbbVie Inc., North Chicago, IL (US)

(72) Inventors: James J. Hughes, Libertyville, IL (US); Bhimaprasad Medhal, Lake Forest, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 15/906,371

(22) Filed: Feb. 27, 2018

(65) Prior Publication Data
US 2018/0250470 A1 Sep. 6, 2018

Related U.S. Application Data

(60) Provisional application No. 62/465,480, filed on Mar. 1, 2017.

(51) Int. Cl.
*A61M 5/20* (2006.01)
*A61M 5/50* (2006.01)
*A61M 5/31* (2006.01)

(52) U.S. Cl.
CPC .............. *A61M 5/20* (2013.01); *A61M 5/50* (2013.01); *A61M 5/5086* (2013.01); *A61M 2005/206* (2013.01); *A61M 2005/3125* (2013.01); *A61M 2205/3561* (2013.01); *A61M 2205/3569* (2013.01); *A61M 2205/58* (2013.01); *A61M 2205/6027* (2013.01)

(58) Field of Classification Search
CPC ........ A61M 5/20; A61M 5/50; A61M 5/5086; A61M 2205/3561; A61M 2205/3569; A61M 2205/6027
See application file for complete search history.

(56) References Cited

U.S. PATENT DOCUMENTS 3,910,260 A  10/1975 Sarnoff et al.
3,941,130 A   3/1976 Tibbs
(Continued)

FOREIGN PATENT DOCUMENTS

WO    WO 2016/055305 A1    4/2016

OTHER PUBLICATIONS

International Search Report and Written Opinion dated Jun. 6, 2018 in International Application No. PCT/US2018/019892.

*Primary Examiner* — Bradley J Osinski
(74) *Attorney, Agent, or Firm* — Baker Botts L.L.P.

(57) ABSTRACT

A automatic injection device including a housing, a firing mechanism, a near-field communication (NFC) assembly, a syringe, and a plunger. The firing mechanism is disposed within the second end of the housing and includes an activation button moveable relative to the firing body between an initial position and an actuated position. The activation button is configured to deploy the plunger when actuated. The firing mechanism includes a piercing element extending from at least the firing body or the activation button. The NFC assembly includes a film disposed proximate the piercing element and configured to be pierced by the piercing element upon actuation of the activation button. The NFC circuit is configured to indicate a film status including at least an unpierced film status before the film is pierced and a pierced film status after the film is pierced. A method of using the automatic injection device is also disclosed.

22 Claims, 18 Drawing Sheets

(56) References Cited

U.S. PATENT DOCUMENTS

| | | |
|---|---|---|
| 4,004,577 A | 1/1977 | Sarnoff |
| 4,261,358 A | 4/1981 | Vargas et al. |
| 4,689,042 A | 8/1987 | Sarnoff et al. |
| 4,755,169 A | 7/1988 | Sarnoff et al. |
| 4,795,433 A | 1/1989 | Sarnoff |
| 5,085,642 A | 2/1992 | Sarnoff et al. |
| 5,092,843 A | 3/1992 | Monroe et al. |
| 5,102,393 A | 4/1992 | Sarnoff et al. |
| 5,267,963 A | 12/1993 | Bachynsky |
| 6,149,626 A | 11/2000 | Bachynsky et al. |
| 6,270,479 B1 | 8/2001 | Bergens et al. |
| 6,371,939 B2 | 4/2002 | Bergens et al. |
| 8,679,061 B2 | 3/2014 | Julian et al. |
| 8,992,476 B2 | 3/2015 | Shang et al. |
| 2014/0207073 A1 | 7/2014 | Shang et al. |
| 2014/0296824 A1 | 10/2014 | Edwards et al. |
| 2015/0057613 A1 | 2/2015 | Clemente et al. |
| 2017/0235920 A1* | 8/2017 | Bauss ................ G06F 19/3462 705/2 |

\* cited by examiner

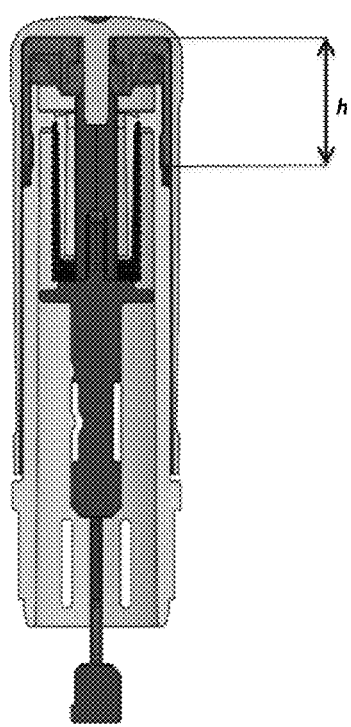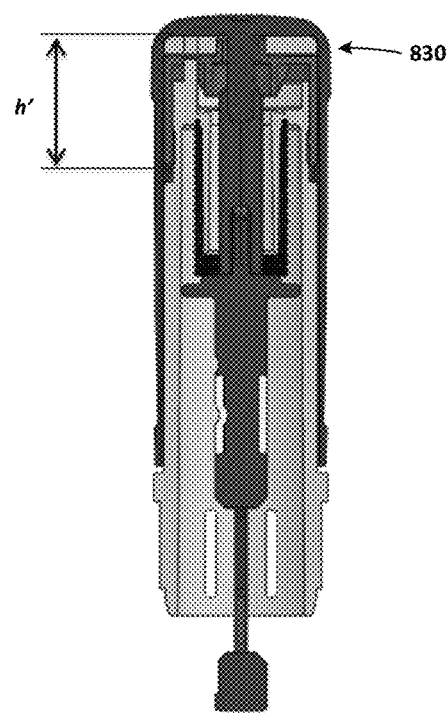
FIG. 6A                    FIG. 6B

AUTOMATIC INJECTION DEVICE WITH NEAR-FIELD COMMUNICATION

RELATED APPLICATION

This application claims the benefit of U.S. Provisional Application No. 62/465,480, filed Mar. 1, 2017, the entire contents of which are incorporated herein in its entirety.

BACKGROUND

Field of the Disclosed Subject Matter

The present disclosed subject matter relates to an automatic injection device for injecting a substance, such as a therapeutic agent, into a patient, and particularly an activation assembly for deploying the same.

Description of Related Art

One of the most common routes of administration for therapeutic agents, such as medications, is by injection, such as intravenous, subcutaneous or intramuscular injection. A syringe containing the medication is used for the injection, which is typically carried out by trained medical personnel. In certain circumstances, a patient may be trained in the use of the syringe to allow for self-injection. Moreover, certain medications are formulated in pre-filled syringes for patient use, to avoid the need for the patient to fill the syringe. Some patients, however, can be averse to carrying out self-injection, particularly if the patient has a fear of needles or limited dexterity.

Automatic injection devices offer an alternative to a syringe for delivering a therapeutic agent. Automatic injection devices have been used, for example, to deliver medications under emergency conditions, such as to administer epinephrine to counteract the effects of a severe allergic reaction, for example, as caused by a food allergy. Automatic injection devices have also been described for use in administering antiarrhythmic medications and selective thrombolytic agents during a heart attack (see e.g., U.S. Pat. Nos. 3,910,260; 4,004,577; 4,689,042; 4,755,169 and 4,795,433). Various types of automatic injection devices also are described in, for example, U.S. Pat. Nos. 3,941,130; 4,261,358; 5,085,642; 5,092,843; 5,102,393; 5,267,963; 6,149,626; 6,270,479; 6,371,939; and 8,992,476, each of which is incorporated by reference herein in its entirety.

As for the use of automatic injection devices for self-injection by patients, there is an increasing need for authentication, tamper evidence and confirmation of adherence to enhance safety and efficacy of medications delivered to the patient.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, a firing mechanism assembly for an automatic injection device is provided, including a firing body and an activation button moveable relative to the firing body between an initial position and an actuated position. The activation button is configured to deploy a plunger when moved to the actuated position. The firing mechanism assembly further includes a piercing element extending from at least one of the firing body and the activation button. The firing mechanism further includes a near-field communication (NFC) assembly comprising a film disposed proximate the piercing element configured to be pierced by the piercing element upon actuation of the activation button to the actuated position, and an NFC circuit configured to indicate a film status including at least an unpierced film status before the film is pierced and a pierced film status after the film is pierced.

Additionally, and as embodied herein, the piercing element can extend from the firing body, wherein at least a portion of the NFC assembly is carried by the activation button. For example, the activation button can have an aperture defined therein to receive the piercing element when the activation button is moved to the actuated position. The film can be aligned with the aperture to be pierced by the piercing element when the activation button is moved to the actuated position.

As embodied herein, the NFC assembly can include a film support member with the film mounted thereon. The film support member can have an aperture defined therein in alignment with the aperture of the activation button configured to receive the piercing element at least partially therein when the activation button is moved to the actuated position. The film can be attached to the film support member using adhesive bonding, in-mold labelling, or laser welding. Furthermore, the film can include a first film portion on a first side of the film support member and a second film portion on a second side of the film support member. Additionally, an activation button cap can be used to secure the film support member on the activation button. In addition, the NFC circuit can be disposed on the film.

As embodied herein, a portion of the NFC circuit is configured to be disabled when the film is pierced by the piercing element to indicate the pierced film status, where the pierced film status corresponds to the firing mechanism assembly being unacceptable for use.

In addition, and as embodied herein, the NFC circuit can include a passive electronic circuit that contains authentication information configured to be machine readable when energized by an external energy source. For example, the NFC circuit can include a first circuit configured to be disabled when the activation button is moved to the actuated position and a second circuit configured to contain the authentication information.

In accordance with another aspect of the disclosed subject matter, an automatic injecting device is provided, including a syringe disposed within a syringe housing assembly and configured to be deployed from an initial condition to a deployed condition. A firing mechanism is coupled with the syringe housing assembly and configured when actuated to deploy the syringe from the initial condition to the deployed condition. The firing mechanism includes a piercing element. The automatic injection device further includes an NFC assembly including a film disposed proximate the piercing element and configured to be pierced by the piercing element upon actuation of the firing mechanism, and an NFC circuit configured to indicate a film status including at least an unpierced film status before the film is pierced and a pierced film status after the film is pierced. In addition, and as embodied herein, the syringe can include a reservoir having a therapeutic agent disposed therein.

Additionally, a portion of the NFC circuit can be configured to be pierced by the piercing element to indicate the pierced film status, wherein the pierced film status indicates the automatic injection device is unacceptable for use. As embodied herein, the NFC circuit can include a passive electronic circuit that contains authentication information configured to be machine readable when energized by an external energy source. For example, and as embodied herein, the NFC circuit can include a first circuit configured to be disabled when the firing mechanism is actuated and a second circuit configured to remain enabled when the film is pierced by the piercing element, the authentication information being contained on the second circuit.

In accordance with another aspect of the disclosed subject matter, a method of using a medical device is provided. The method includes exposing the medical device to a remote energy source. The medical device includes a firing mechanism assembly configured when actuated to deploy the medical device from an initial condition to a deployed condition. The firing mechanism assembly includes a piercing element and an NFC assembly including a film disposed proximate the piercing element and configured to be pierced by the piercing element upon actuation of the firing mechanism assembly, and an NFC circuit configured, when energized by the remote energy source, to indicate a film status including at least an unpierced film status before the film is pierced and a pierced film status after the film is pierced. The method further includes receiving a signal generated from the NFC assembly indicating whether the film status is the pierced film status or the unpierced film status, and displaying the film status based upon the signal received from the NFC assembly.

Additionally, and as embodied herein, the film status can be displayed as a message indicating the medical device is in the initial condition if the unpierced film status is received or that the medical device is in the deployed condition if the pierced film status is received.

Furthermore, the NFC circuit can include a passive electronic circuit that contains authentication information configured to be machine readable when energized by the energy source. The method thus can further include receiving the authentication information for the NFC circuit and displaying an approved message if the authentication information is recognized or an unapproved message if the authentication information is not recognized. In addition, and as embodied herein, the method can further include creating a time stamp upon confirmation of deployment of the medical device.

As embodied herein, the displayed film status can be performed on a user interface. In addition, and as embodied herein, displaying the film status can include transmitting the film status to a remote server.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the disclosed subject matter. Together with the description, the drawings serve to explain the principles of the disclosed subject matter.

BRIEF DESCRIPTION OF THE DRAWINGS

FIG. 6A is a cross-sectional side view of a firing mechanism assembly without an NFC assembly.

FIG. 6B is a cross-sectional side view of a firing mechanism assembly with an NFC assembly in accordance with the disclosed subject matter for the purpose of comparison with FIG. 6A.

DETAILED DESCRIPTION OF THE PREFERRED EMBODIMENT

Figure 1:
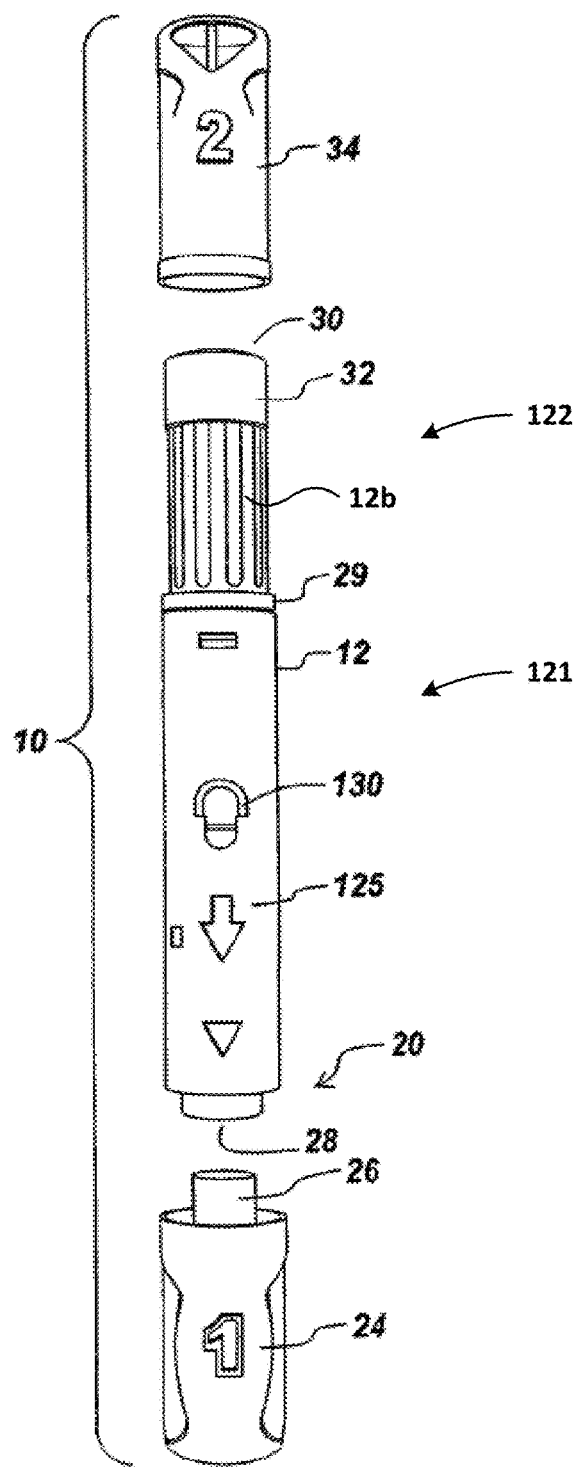
FIG. 1 is an exploded view of an automatic injection device having a firing mechanism assembly and a syringe housing assembly, according to embodiments of the disclosed subject matter.

Reference will now be made in detail to the various exemplary embodiments of the disclosed subject matter, exemplary embodiments of which are illustrated in the accompanying drawings. The structure and corresponding method of operation of the disclosed subject matter will be described in conjunction with the detailed description of the system.

In accordance with aspects of the disclosed subject matter, and as embodied herein, a firing mechanism assembly is provided, including a firing body and an activation button moveable relative to the firing body between an initial position and an actuated position. The activation button is configured to deploy a plunger when moved to the actuated position. The firing mechanism assembly further includes a piercing element extending from at least one of the firing body and the activation button. The firing mechanism further includes a near-field communication (NFC) assembly comprising a film disposed proximate the piercing element configured to be pierced by the piercing element upon movement of the activation button, and to the actuated position and an NFC circuit configured to indicate a film status including at least an unpierced film status before the film is pierced and a pierced film status after the film is pierced.

The accompanying figures, where like reference numerals refer to identical or functionally similar elements throughout the separate views, serve to further illustrate various embodiments and to explain various principles and advantages all in accordance with the disclosed subject matter. For purpose of explanation and illustration, and not limitation, exemplary embodiments of the automatic injection device and firing mechanism assembly are shown in FIGS. 1-19, in accordance with aspects of the disclosed subject matter. While the present disclosed subject matter is described regarding possible embodiments, one skilled in the art will recognize that components and the method of using the same are not limited to the illustrative embodiments described or depicted herein.

Generally, and unless otherwise noted, the term "first end" or "distal end" refers to the portion or end of an automatic injection device or component in the automatic injection device to be disposed or positioned at or near to an injection site when the device is held for an injection or for mimicking an injection. The term "second end" or "proximal end" refers to the portion or end of an automatic injection device or a component of the automatic injection device spaced from an injection site during an injection. An "automatic injection device" or "autoinjector" is intended to refer generally to a device that enables an individual to administer a dosage of a liquid substance (e.g., a therapeutic liquid substance) to an injection site.

Solely for purpose of illustration, with reference to FIG. 1, an automatic injection device 10 is provided. The automatic injection device 10 includes a syringe housing assembly 121 coupled to a firing mechanism assembly 122. The firing mechanism assembly 122 is configured, when actuated, to deploy a syringe disposed within the syringe housing assembly 121, from an initial condition to a deployed condition. Further details of the automatic injection device 10, and particularly the syringe housing assembly 121, will be described with reference to FIGS. 8-10B. Further details of the firing mechanism assembly 122 will now be described with reference to FIGS. 2-7.

Referring now to FIGS. 2-5, the firing mechanism assembly 122 is provided, according to aspects of the disclosed subject matter. For example, and as embodied herein, the firing mechanism assembly 122 includes a firing body 12b and an activation button 32 moveable relative to the firing body 12b between an initial position and an actuated position. The activation button 32 is configured to deploy a plunger 700 when moved to the actuated position. The firing mechanism assembly 122 includes a piercing element 831 extending from at least one of the firing body 12b and the activation button 32. For example, and as embodied herein for illustration and not limitation, the piercing element 831 can extend from the firing body 12b. The firing mechanism assembly 122 further includes an NFC assembly 830 including a film 832 disposed proximate the piercing element 831, and configured to be pierced by the piercing element 831 upon movement of the activation button 32 to the actuated position, and an NFC circuit 834 configured to indicate a film status including at least an unpierced film status before the film 832 is pierced and a pierced film status after the film 832 is pierced.

According to aspects of the disclosed subject matter, the film 832 can be any suitable material capable of supporting NFC communication between the NFC circuit 834 and an external NFC device, such as a mobile device (e.g., a smart phone). For example, the film 832 can be a conductive material used to transmit data or a non-conductive material used as a substrate for a conductive material. Furthermore, the film 832 can be any suitable shape, such as a disk configured to fit within a tubular firing body 12b as illustrated. For example, and not as a limitation, the disk can have a diameter of about 15 mm and a thickness of about 3 mm. The film 832 can also have an inner opening configured to receive, for example, a connecting link between a cap and the activation button 32 for deployment of the plunger 700.

Furthermore, and as embodied herein, the NFC circuit 834 can include one or more circuits each including a material capable of facilitating communication between the NFC assembly 830 and, for example, an external NFC device. Communication can be initiated by an external power source that energizes the NFC circuit 834 using electromagnetic power suitable for NFC technology. When the NFC circuit 834 is energized, the NFC circuit 834 can be configured to transmit a film status to the external NFC device, the external power source, or any other device capable of receiving an NFC signal. The film status can indicate an unpierced film status (e.g., the state of the film 832 before actuation of the activation button 32) or a pierced film status (e.g., the state of the film 832 after actuation of the activation button 32).

As embodied herein, for illustration and not limitation, the piercing element 831 can extend from the firing body 12b, and at least a portion of the NFC assembly 830 can be carried by the activation button 32. Generally, the term "carried" as used herein refers to a positional relationship between components and a coupled movement between said components. For example, the NFC assembly 830 can be disposed proximate a top surface of the activation button 32 such that the NFC assembly 830 travels with (e.g., is carried by) the activation button 32 between the initial position and the actuated position.

Additionally, and as embodied herein, the activation button can have an aperture 833 defined therein to receive the piercing element 831 when the activation button 32 is moved from the initial position to the actuated position, according to aspects of the disclosed subject matter. The portion of the NFC assembly 830 carried by the activation button 32 can include the film 832, such that the film 832 is aligned with the aperture 833 to be pierced by the piercing element 831. For example, the piercing element 831 can be attached to the firing body 12b, as described above, such that the piercing element 831 passes through the aperture 833 and pierces the film 832 when the activation button 32 is moved from the initial position to the actuated position.

Figure 3A:
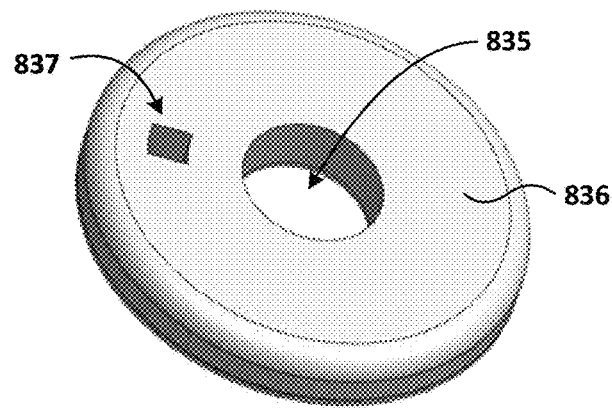
FIG. 3A is an isometric top view of a film and film support member used in the firing mechanism assembly of FIG. 1, according to embodiments of the disclosed subject matter.
Figure 3B:
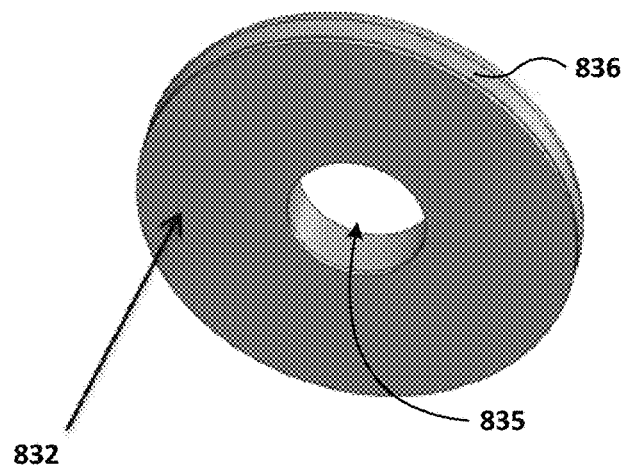
FIG. 3B is an isometric bottom view of the film and film support member of FIG. 3A, according to embodiments of the disclosed subject matter.
Figure 4A:
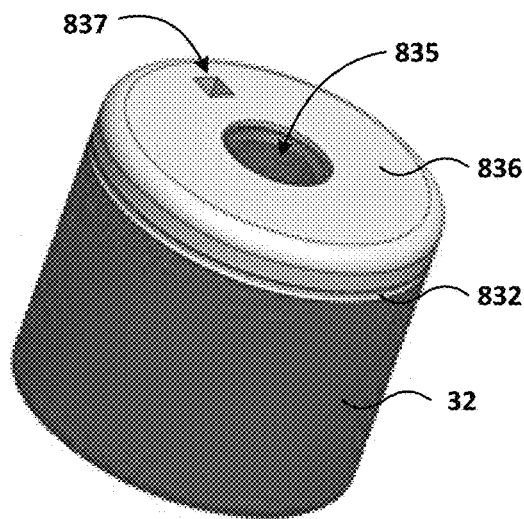
FIG. 4A is an isometric top view of the film and film support member of FIG. 3A and an activation button used in the firing mechanism assembly of FIG. 1, according to embodiments of the disclosed subject matter.
Figure 4B:
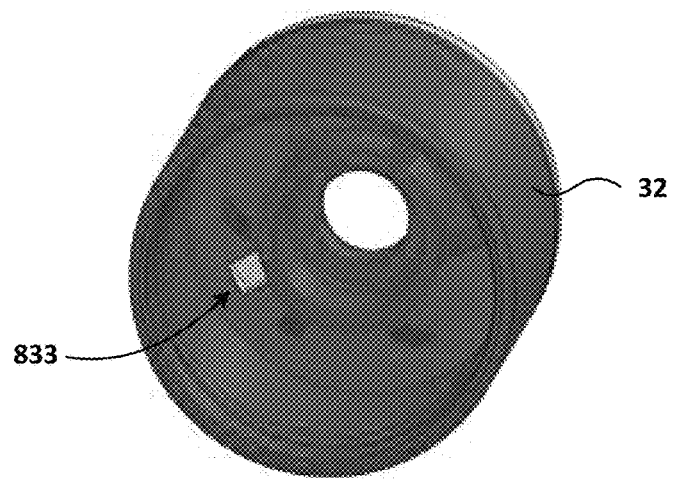
FIG. 4B is an isometric bottom view of the activation button, the film, and the film support member of FIG. 4A, according to embodiments of the disclosed subject matter.

According to further aspects of the disclosed subject matter, the NFC assembly 830 can include a film support member 836 with the film 832 attached or mounted thereon, as depicted for example in FIGS. 3A-3B. The film support member 836 can have an aperture 837 defined therein and in alignment with the aperture 833 of the activation button 32 so as to receive the piercing element 831 at least partially therein when the activation button 32 is moved from the initial position to the actuated position. For example, the piercing element 831 can pass through the aperture 833 and pierce the film 832 when the activation button 32 is moved from the initial position to the actuated position, as described above. Additionally, the piercing element 831 can pass through a portion of the aperture 837 after piercing the film 832. Additional movement of the piercing element 831 after piercing the film 832 (e.g., the movement into the aperture 837) can provide additional space to facilitate the piercing element 831 fully piercing the film 832.

Additionally, and as embodied herein, the film 832 can be attached to the film support member 836 using adhesive bonding, in-mold labelling, or laser welding. For example, an adhesive bonding technique can be used such that an adhesive is applied directly to a top surface of the film 832, which is then coupled to a bottom surface of the film support member 836.

Figure 2:
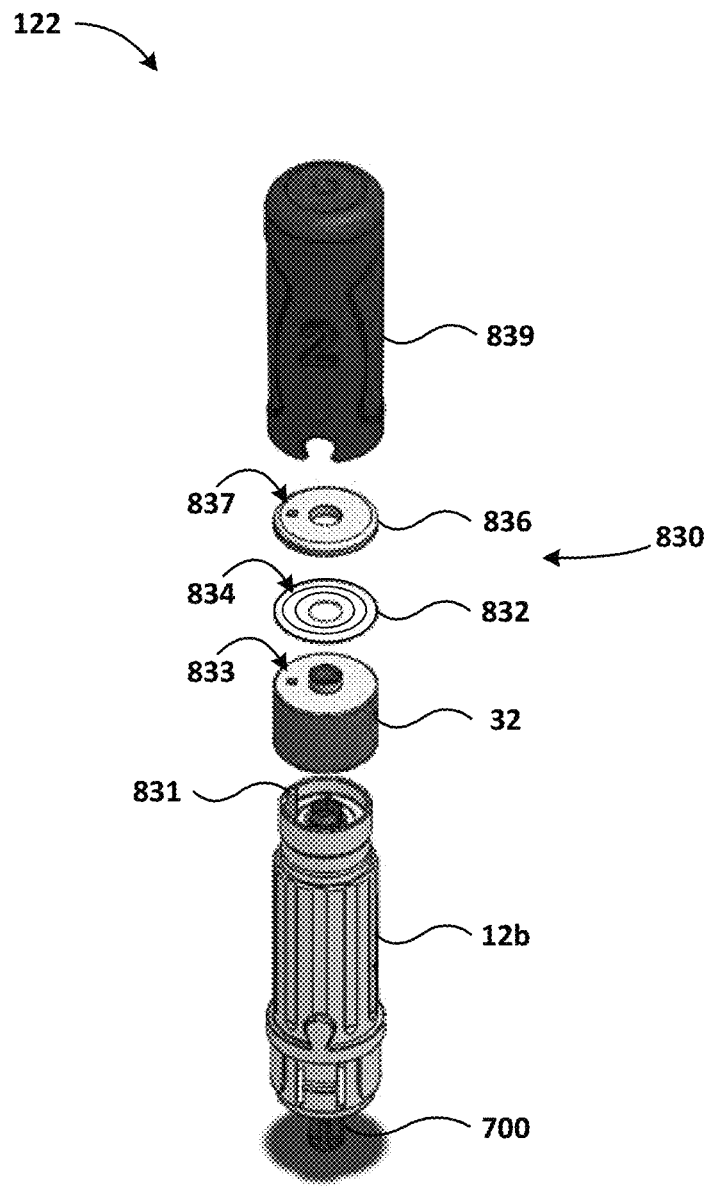
FIG. 2 is an exploded view of the firing mechanism assembly of FIG. 1, according to embodiments of the disclosed subject matter.
Figure 5:
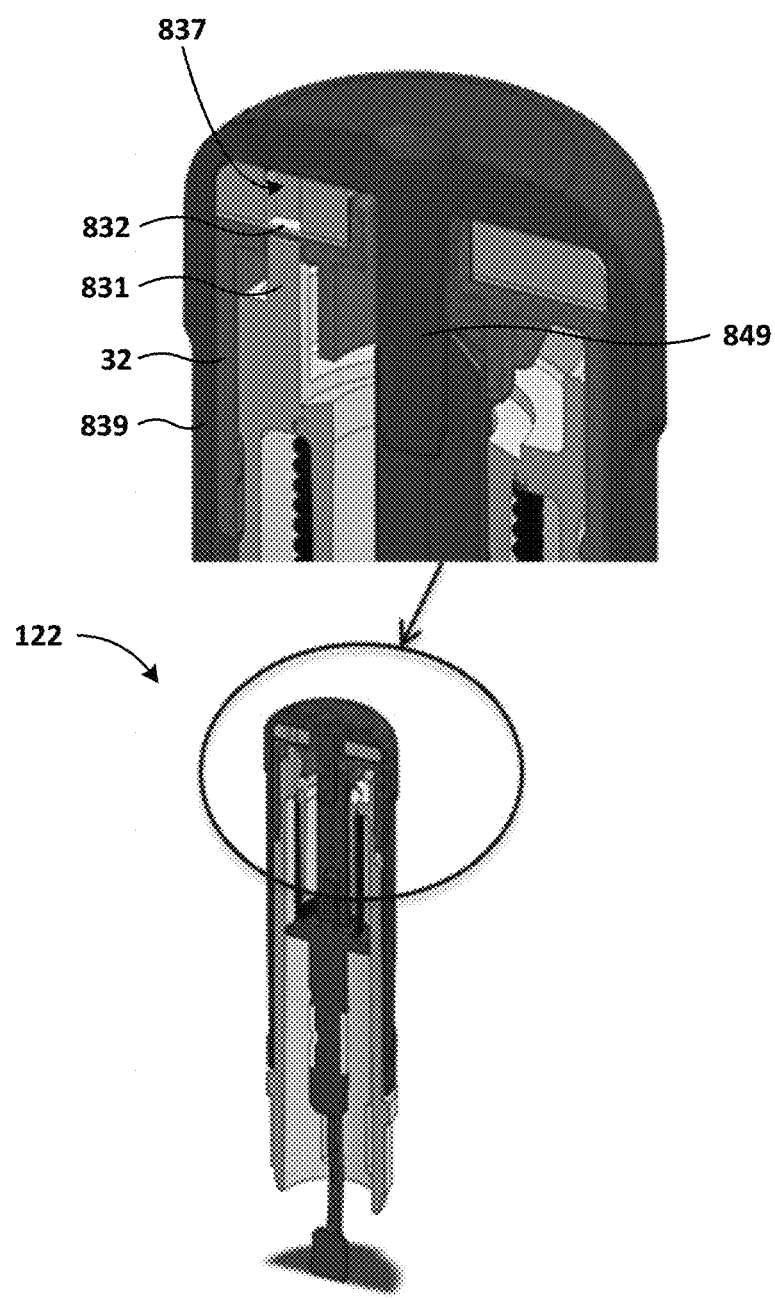
FIG. 5 is a cross-sectional detail view of the firing mechanism assembly of FIG. 1, according to embodiments of the disclosed subject matter.

Furthermore, and as depicted for example in FIGS. 2 and 5, the firing mechanism assembly 122 can also include an activation button cap 839, which can secure the film support member 836 to the activation button 32. For example, the activation button cap 839 can include a connector element 849 configured to secure the film support member 836 to the activation button 32 in any suitable manner. In one example, as shown in FIG. 5, the connector element 849 extends through a center hole 835 of the film support member 836 and film 832 connecting to the activation button 32 and/or in engagement with plunger 700 for deployment.

According to further aspects of the disclosed subject matter, at least a portion of the NFC circuit 834 can be disposed on a portion of the film 832. The NFC circuit 834 can be formed or bonded on the film 832 using any suitable techniques, such as with an adhesive or by material printing.

With continued reference to FIGS. 2-5, and according to further aspects of the disclosed subject matter, at least a portion of the NFC circuit 834 is configured to be disabled when the film 832 is pierced by the piercing element 831 to indicate a pierced film status. For example, a portion of the NFC circuit 834 can be aligned with aperture 833, such that the piercing element 831 breaks, opens, or disconnects said portion of the NFC circuit 834 when the activation button 32 is moved from the initial position to the actuated position.

According to further aspects of the disclosed subject matter, the NFC circuit 830 can include a passive electronic circuit having authentication information configured to be machine readable when energized by an external energy source. For example, the authentication information can be information relating to the authenticity of the automatic injection device 10 or the contents therein. The authentication information can be configured by, for example, the manufacturer having a unique identification tag or serial number such that the machine-readable device can identify the automatic injection device 10 as being genuine or authentic.

A variety of suitable configurations for the NFC circuit 834 can be used, in accordance with the disclosed subject matter. As embodied herein, the NFC circuit 834 can include a first circuit configured to be disabled when the activation button is moved to the actuated position and a second circuit configured to contain the authentication information, according to aspects of the disclosed subject matter.

To achieve the above mentioned configuration, the NFC circuit 834 can be formed as one or more conductive circuits, such as one or more copper wire circuits formed on a surface of the film 832. For illustration and not limitation, each conductive wire circuit can include one or more informational data sets or packets. For example, the film status can be transmitted in the form of a data packet from the NFC assembly 830 to an external device. The unpierced film status can be communicated by a first circuit of the NFC circuits 834, while an authentication film status can be communicated by a second circuit of the NFC circuits 834. The first circuit can be configured to break when the activation button 32 is moved from the initial position to the actuated position by, for example, aligning the first circuit in an actuation path of the piercing element 831. Prior to actuation of the activation button 32, both circuits are closed (e.g., unbroken or intact), the external power source energizes both circuits, and an unpierced film status and an authentic film status is each transmitted to the external NFC device by the first circuit and the second circuit, respectively. The activation button 32 is actuated, piercing the film and breaking the first circuit. The external power source is then placed proximate the NFC assembly 830 energizing the second circuit, thereby effectively communicating two statuses of the film. The first film status is communicated by the absence of a signal from the first circuit, and the second film status is communicated by the transmission from the second circuit. Further details of the method of using the firing mechanism assembly 122, including the method of using the automatic injection device 10, are further described with reference to FIGS. 11-14.

The firing mechanism assembly of the disclosed subject matter thus can be provided with an NFC assembly with minimal conversion or additional material or space required. Solely for purpose of illustration and comparison, reference is now made to FIGS. 6A and 6B, in which a cross-sectional schematic of an automatic injection device without an NFC assembly (FIG. 6A), and with an NFC assembly 830 in accordance with the disclosed subject matter (FIG. 6B). For example, in FIG. 6A, the automatic injection device without an NFC assembly 830 is illustrated with an activation button height (h), and in FIG. 6B, the automatic injection device with the NFC assembly 830 is illustrated with an activation button height (h'). For example, and according to aspects of the disclosed subject matter, (h) is equal to (h'), and as embodied herein, each is generally equal to about 14.6 mm. That is, with limited modification, activation buttons of existing automatic injection devices can be modified to accommodate the NFC assembly 830 of the disclosed subject matter, maintaining overall device dimensions.

Figure 7:
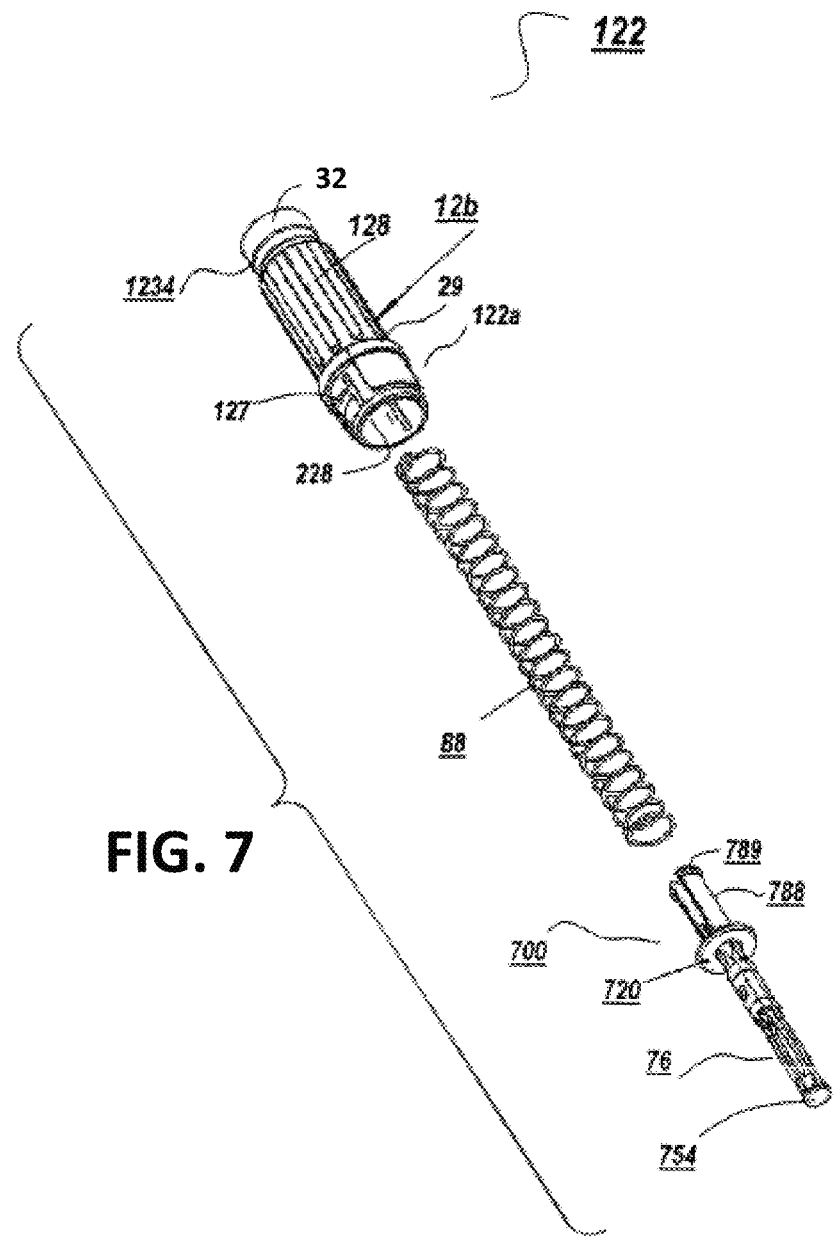
FIG. 7 is an exploded view of the firing mechanism assembly of FIG. 1, according to embodiments of the disclosed subject matter.

Solely for purpose of illustration, reference is now made to FIG. 7, in which an exploded view of the firing mechanism assembly 122 is illustrated, according to aspects of the disclosed subject matter. As shown, the firing mechanism assembly 122 includes the activation button 32, the firing body 12b and a coil spring 88 or other biasing mechanism used to deploy the plunger 700 when the activation button 32 is moved from the initial position to the actuated position. The plunger 700 extends from a first end 122a of the firing body 12b. As embodied herein, the plunger 700 can be configured to move a syringe from an initial condition to a deployed condition as well as to further move distally to expel the contents of the syringe. For purpose of illustration and not limitation, reference to the operation and components of the plunger 700 and coil spring 88 are further described in, for example, U.S. Pub. No. 2014/0207073 and U.S. Pat. No. 8,679,061, each of which is incorporated by reference herein in its entirety.

Figure 8:
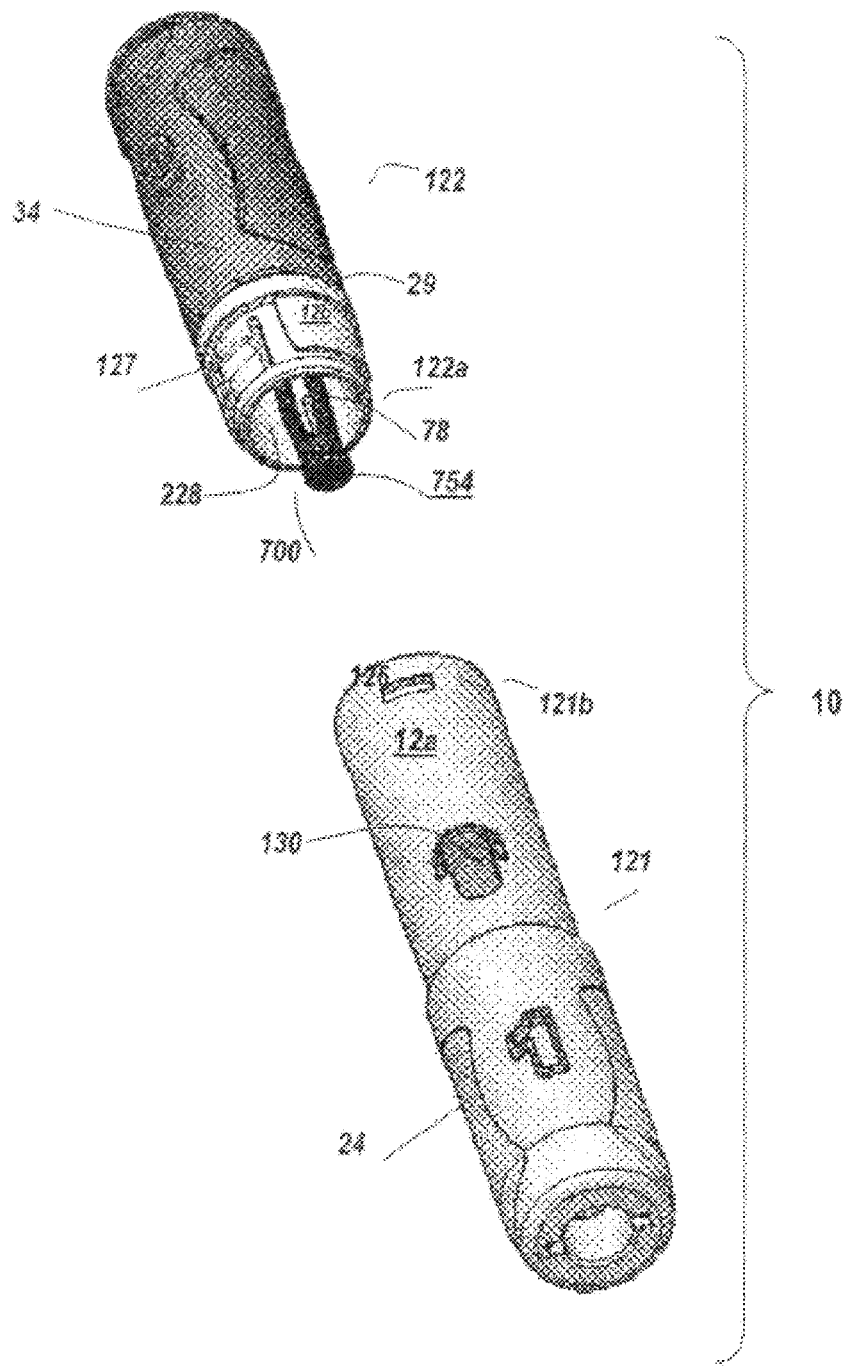
FIG. 8 is an exploded view of the firing mechanism assembly and syringe housing assembly of FIG. 1, according to embodiments of the disclosed subject matter.
Figure 9:
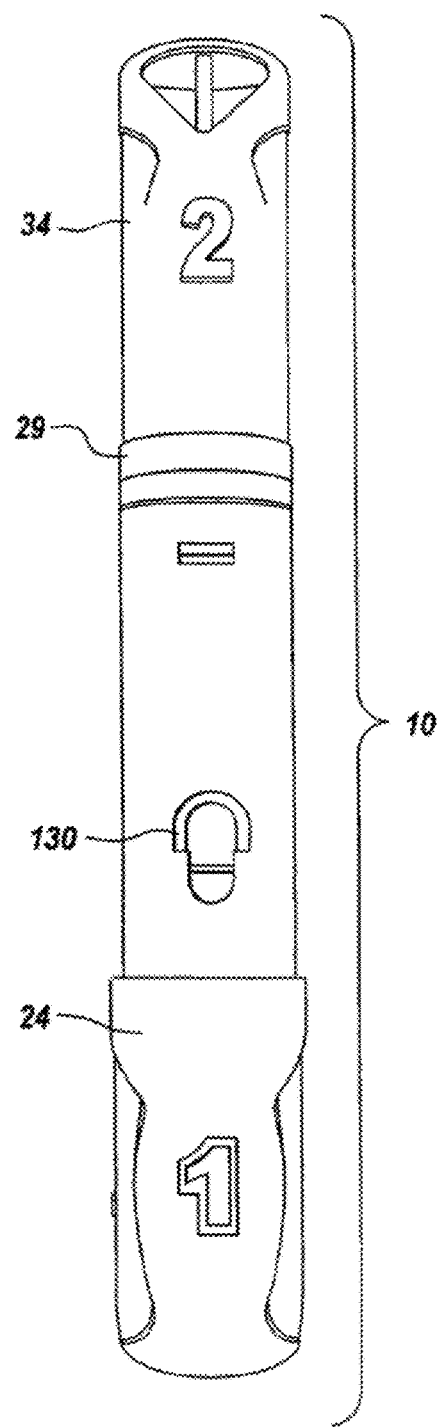
FIG. 9 is a side view of the automatic injection device of FIG. 1, according to embodiments of the disclosed subject matter.

With reference now to FIG. 8, the firing mechanism assembly 122 can be coupled with the syringe housing assembly 121 by interlocking the assemblies using any suitable coupling to form the automatic injection device 10 depicted in FIG. 9. For example, a first end 122a of the firing mechanism assembly 122 can be sized and configured to be inserted into a second end 121b of the syringe housing assembly 121. In addition, one or more tabs 127 on the first end 122a of the firing mechanism assembly 122 can snap-fit into corresponding openings 126 on the second end 121b of the syringe housing assembly 122 to align and couple the two assemblies 121, 122 and the components housed therein. Further details of the automatic injection device 10 and components therein will now be described with reference to FIGS. 1 and 8-10B.

In accordance with another aspect of the disclosed subject matter, and as embodied herein, an automatic injection device is provided, including a syringe disposed within a syringe housing assembly and configured to be deployed from an initial condition to a deployed condition. A firing mechanism is coupled with the syringe housing assembly and configured when actuated to deploy the syringe from the initial condition to the deployed condition. The firing mechanism includes a piercing element. The automatic injection device further includes an NFC assembly comprising a film disposed proximate the piercing element and configured to be pierced by the piercing element upon actuation of the firing mechanism, and an NFC circuit configured to indicate a film status including at least an unpierced film status before the film is pierced and a pierced film status after the film is pierced.

Solely for purpose of illustration, reference is now made to FIGS. 1 and 8-10B, in which an automatic injection device 10 is provided, according to aspects of the disclosed subject matter. For example, the automatic injection device 10 includes a syringe 50 disposed within the syringe housing assembly 121 configured to be deployed from an initial condition to a deployed condition. The firing mechanism assembly 122 coupled with the syringe housing assembly 121 are configured when actuated to deploy the syringe 50 from the initial condition to the deployed condition. The firing mechanism assembly 122 includes the piercing element 831. The automatic injection device 10 further includes the NFC assembly 830 including the film 832 disposed proximate the piercing element 831 and configured to be pierced by the piercing element 831 upon actuation of the firing mechanism assembly 122, and an NFC circuit 834 configured to indicate a film status including at least an unpierced film status before the film 832 is pierced and a pierced film status after the film 832 is pierced. Additional details of the firing mechanism assembly 122 are described herein, with reference to the automatic injection device.

The firing mechanism assembly 122 is disposed in housing 12 and includes the activation button 32, which is engaged with plunger 700 exposed through a second end 30 of the housing 12. The activation button 32 can be used to deploy the syringe 50 from an initial condition within the housing 12 to a deployed condition, such that the needle of the syringe 50 projects from the housing and expels a substance from the syringe 50 into a patient. The syringe 50 can be deployed using aspects of the firing mechanism assembly 122 described above. The syringe housing assembly 121 is described further in reference to FIGS. 10A and 10B.

Referring now to FIGS. 1, 8, and 9, the housing 12 generally has a tubular configuration and is composed of a suitable surgical or medical device material such as plastic, though one skilled in the art will recognize that the housing 12 can have any number of shapes, configurations, and compositions for housing a syringe or other container of a substance to be injected. As described further below, the housing 12 includes the syringe housing body 12a for housing components of the syringe housing assembly 121 and the firing body 12b for housing components of the firing mechanism assembly 122.

Furthermore, and as embodied herein, the automatic injection device 10 can include a first removable cap 24 to cover the first end 20 of the housing 12, and thus prevent exposure of or access to the needle in the syringe prior to use. As embodied herein, the first cap 24 can include a boss or hub 26 for locking and/or covering the interior components of the device 10 until the user is ready to activate the device 10. Additionally, a second removable cap 34 can be provided to cover the second end 30 of the housing 12 and thus prevent accidental actuation of the activation button 32. For the purpose of illustration and not limitation, reference to the operation and components of the housing 12 and caps 24 and 34 are further described in, for example, U.S. Pub. No. 2014/0207073 and U.S. Pat. No. 8,679,061, each of which is incorporated by reference herein in its entirety.

Figure 10A:
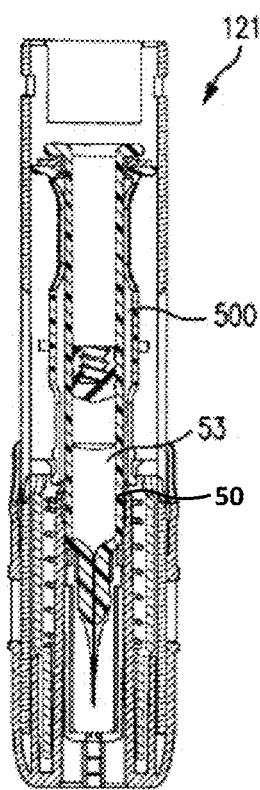
FIG. 10A is a cross-sectional schematic of the syringe housing assembly of FIG. 1, the syringe housing assembly is in a pre-deployment position, according to embodiments of the disclosed subject matter.
Figure 10B:
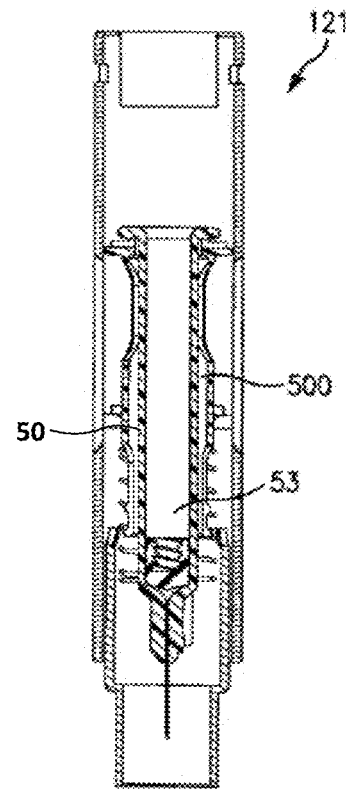
FIG. 10B is a cross-sectional schematic of the syringe housing assembly of FIG. 1, the syringe housing assembly is in a post-deployment position, according to embodiments of the disclosed subject matter.
Figure 11:
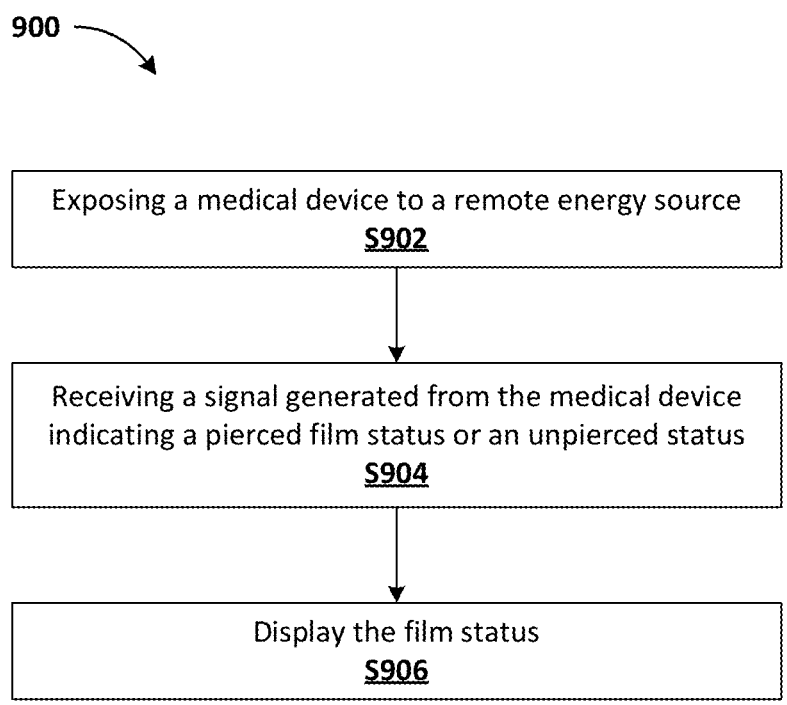
FIG. 11 is an operational flowchart generally depicting the method for using the automatic injection device of FIG. 1, according to embodiments of the disclosed subject matter.

Referring now to FIGS. 10A and 10B, the syringe housing assembly 121 is illustrated schematically to depict general aspects of the disclosed subject matter. The syringe housing assembly 121 includes the syringe 50 having a barrel 53 containing a liquid substance to be injected into a patient. For example, the liquid substance can be a therapeutic agent and can include one or more biological agents, such as a protein. For example and without limitation, the liquid therapeutic agent can be a TNF inhibitor, such as adalimumab. While the disclosed subject matter will be described with respect to the syringe 50 mounted in the housing 12, one skilled in the art will recognize that the automatic injection device 10 can employ other suitable containers and configurations for storing and dispensing a substance. For example, the container for storing and dispensing a substance can be a cartridge. Additionally, the container, whether a syringe or cartridge, can be made of glass, a polymer, or a variety of other suitable materials for storing and dispensing a substance.

The syringe 50 is slidably mounted in the housing 12. In an initial condition, as shown in FIG. 10A, the syringe 50 is sheathed and retracted within the housing 12. When the device is actuated, the syringe 50 is extended such that a needle of the syringe projects from a first end 20 of the housing 12 to allow ejection of a substance from the syringe 50 into a patient. The first end of the housing 20 includes an opening 28 through which the needle of the syringe 50 projects during actuation of the device 10. FIG. 10B illustrates the syringe housing assembly 121 in a deployed condition with the automatic injection device 10 removed from the injection site causing a stepped shroud to deploy. Upon completion of the stroke or movement of the syringe 50, the contents of the syringe 50 are no longer in the barrel 53 of the syringe 50.

As embodied herein, for purpose of illustration and not limitation, a syringe carrier 500 can be provided and configured to hold or contain at least a portion of a syringe 50. The syringe 50 is held by the carrier 500, which in turn is contained in the housing 12. During operation, the syringe 50 and carrier 500 move forward (e.g., towards the first end 20 proximate the injection site) within the housing 12. The housing 12 can be configured to inhibit or prevent the movement of the carrier 500 beyond the first end 20, and the carrier 500 in turn inhibits or prevents the movement of the syringe 50.

For purpose of description and not limitation, reference to the operation and components of the syringe housing assembly 121 are further described in, for example, U.S. Pub. No. 2014/0207073 and U.S. Pat. No. 8,679,061, each of which is incorporated by reference herein in its entirety.

In view of the above, the automatic injection device of the disclosed subject matter can incorporate the components and features of the firing mechanism assembly as described above. For example, and as embodied herein, the automatic injection device can include a passive electronic circuit including authentication information configured to be machine readable when energized by an external energy source. Furthermore, the automatic injection device can include the NFC circuit which can have a first circuit configured to be disabled when the firing mechanism assembly is actuated and a second circuit configured to remain enabled when the film is pierced by the piercing element, and as embodied herein, with the authentication information being contained on the second circuit.

In accordance with another aspect of the disclosed subject matter, and as embodied herein, a method of using a medical device is provided, including exposing the medical device to a remote energy source. The medical device includes a firing mechanism assembly configured when actuated to deploy the medical device from an initial condition to a deployed condition. The firing mechanism assembly includes a piercing element and an NFC assembly comprising a film disposed proximate the piercing element and configured to be pierced by the piercing element upon actuation of the firing mechanism assembly, and an NFC circuit configured, when energized by the remote energy source, to indicate a film status including at least an unpierced film status before the film is pierced and a pierced film status after the film is pierced. The method further includes receiving a signal generated from the NFC assembly indicating whether the film status is the pierced film status or the unpierced film status and displaying the film status based upon the signal received from the NFC assembly.

Solely for purpose of illustration, reference is now made to FIGS. 11-14, in which a method of using a medical device 10 is illustrated, according to an embodiment of the disclosed subject matter. Generally, the method includes exposing the medical device 10 to a remote energy source 11 (S902). As set forth above, the medical device 10, of the disclosed subject matter includes a firing mechanism assembly configured when actuated to deploy the medical device 10 from an initial condition to a deployed condition. The firing mechanism assembly includes a piercing element and an NFC assembly including a film disposed proximate the piercing element so as to be pierced by the piercing element when the firing mechanism assembly is actuated, and an NFC circuit configured, when energized by the remote energy source, to indicate a film status including at least an unpierced film status before the film is pierced and a pierced film status after the film is pierced. The method therefore further includes receiving a signal generated from the NFC assembly indicating whether the film status is the pierced film status or the unpierced film status (S904), and displaying the film status based upon the signal received from the NFC assembly (S906).

Figure 14:
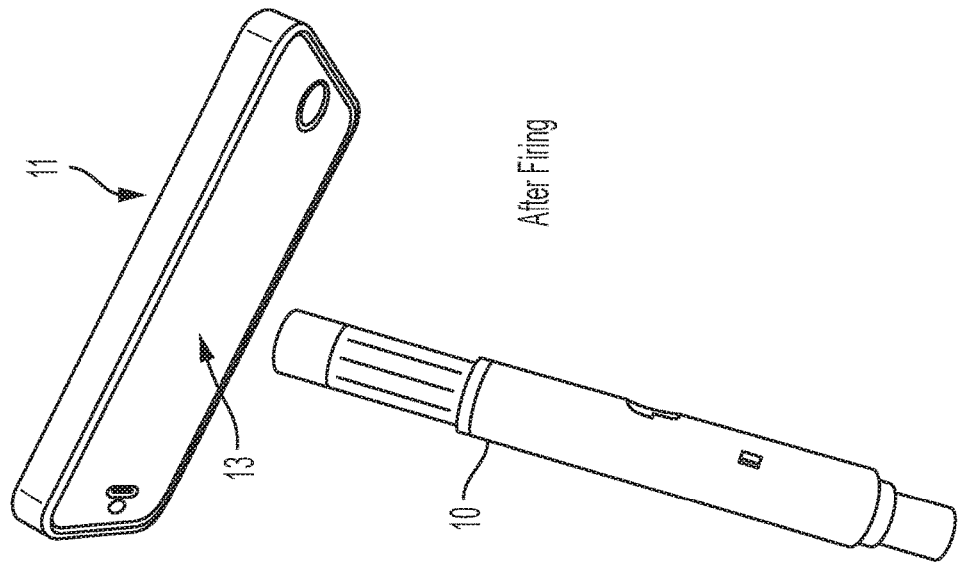
FIG. 14 is an image of the automatic injection device of FIG. 1, with the automatic injection device in a post-deployment position and proximate the remote energy source of FIG. 13, according to embodiments of the disclosed subject matter.
Figure 13:
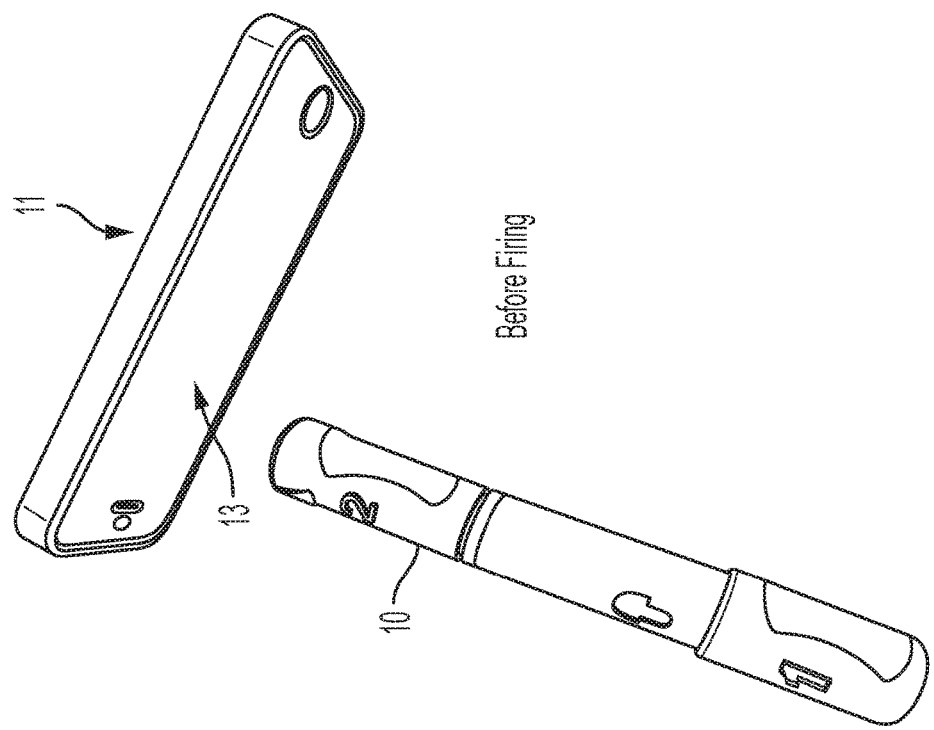
FIG. 13 is an image of the automatic injection device of FIG. 1, with the automatic injection device in a pre-deployment position and proximate a remote energy source, according to embodiments of the disclosed subject matter.
Figure 15A:
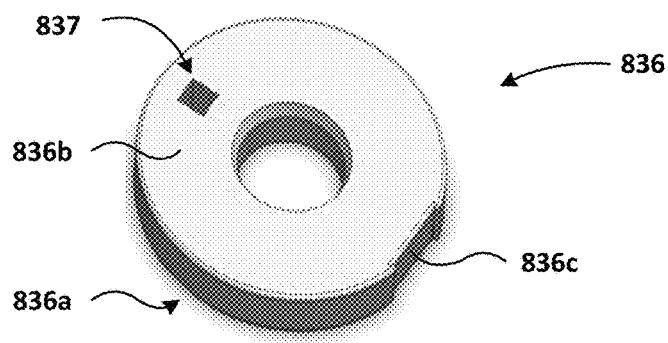
FIG. 15A is an isometric top view of a film support member in the firing mechanism assembly of FIG. 1, according to embodiments of the disclosed subject matter.
Figure 15B:
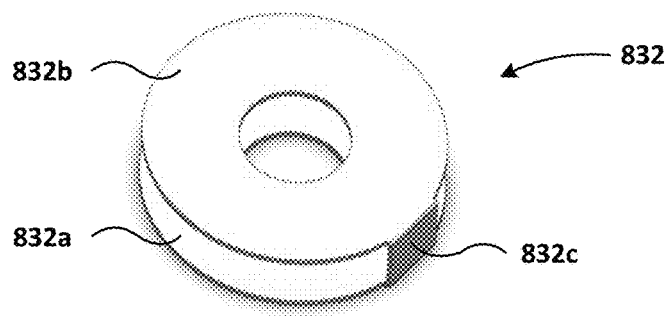
FIG. 15B is an isometric top view of a film in the firing mechanism assembly of FIG. 1, according to embodiments of the disclosed subject matter.
Figure 15C:
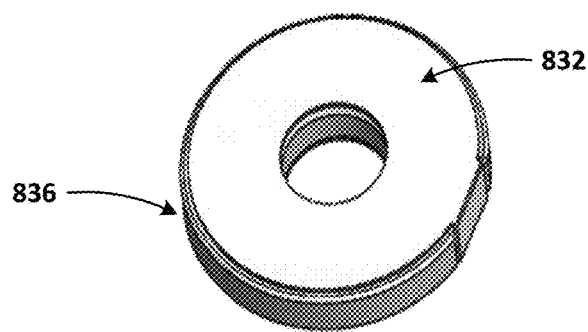
FIG. 15C is an isometric top view of the film and film support member of FIGS. 15A and 15B, according to embodiments of the disclosed subject matter.
Figure 16A:
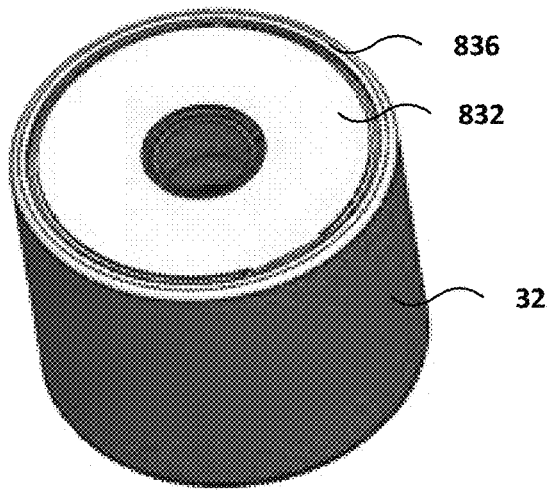
FIG. 16A is an isometric top view of the film and film support member of FIG. 15C and an activation button in the firing mechanism assembly of FIG. 1, according to embodiments of the disclosed subject matter.
Figure 16B:
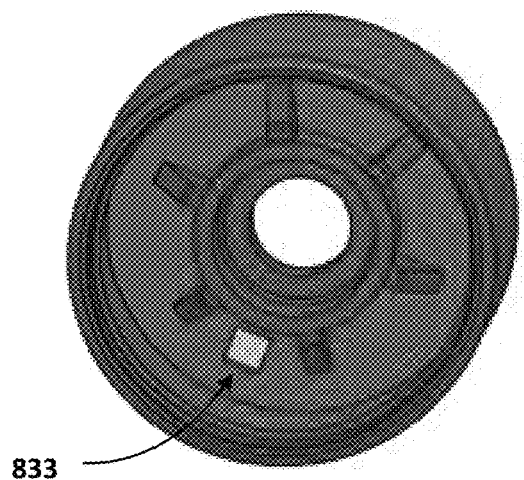
FIG. 16B is an isometric bottom view of the activation button, the film, and the film support member of FIG. 16A, according to embodiments of the disclosed subject matter.
Figure 17:
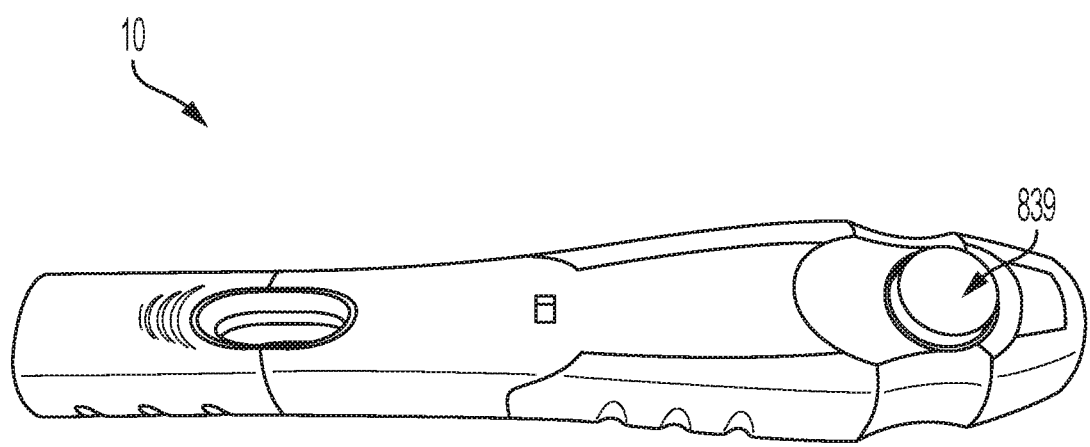
FIG. 17 is an image of an automatic injection device having an activation button on a side of a firing body, according to embodiments of the disclosed subject matter.
Figure 18:
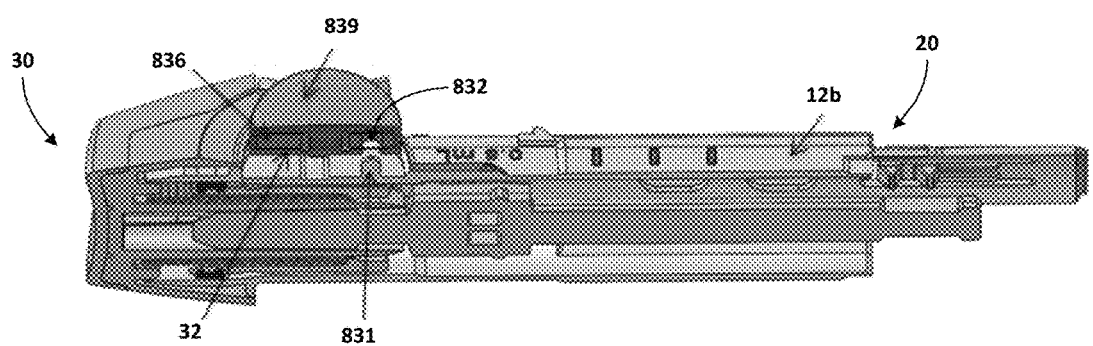
FIG. 18 is a cross-sectional isometric side view of the automatic injection device of FIG. 17, according to embodiments of the disclosed subject matter.
Figure 19:
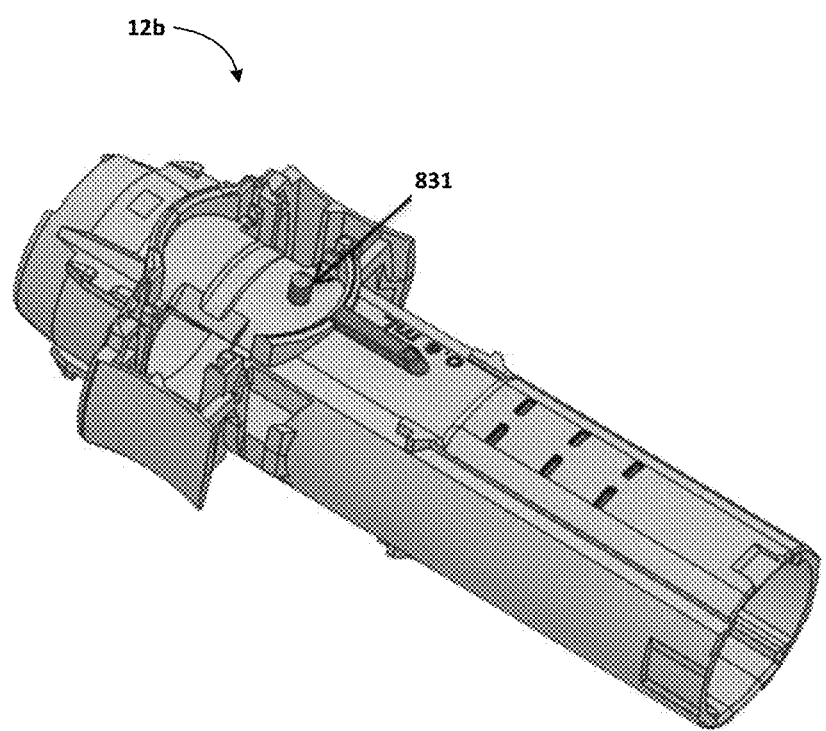
FIG. 19 is an isometric side view of a firing body in the automatic injection device of FIG. 17.

According to aspects of the disclosed subject matter, the medical device 10 can be the same as automatic injection device 10 with the firing mechanism assembly described above. Furthermore, and as depicted in FIGS. 13 and 14 for illustration and not limitation, the remote energy source 11 can be any external power source capable of NFC communication, such as a mobile computing device or mobile phone (e.g., an iPhone® or Android phone).

The method of using the medical device 10 described above can be achieved using NFC technology, which facilitates a two-way interaction between NFC enabled devices without the need for pairing or discovery, in contrast with many other forms of communication protocols between devices. One standardized protocol used for NFC communication includes, for example, ISO 14443 and can be used when two NFC enabled devices are within about four centimeters of each other.

NFC enabled devices can communicate using card emulation, peer-to-peer, or reader/writer modes. NFC enabled devices can also function in an active mode or passive mode. Further description of NFC communication modes and component parts can be found at nfc-forum.org. As applied to aspects of the disclosed subject matter, the medical device 10 and remote energy source 11 communicate in reader/writer mode in a passive capacity, such that an NFC tag (e.g., NFC assembly 830) within the medical device 10 is configured to send a film status to the remote energy source 11 when the remote energy source is proximate the medical device 10.

For example, and according to aspects of the disclosed subject matter, the NFC tag can include one or more NFC circuits which can store information and/or act as an NFC antenna. When the remote energy source is placed proximate the medical device 10, an electromagnetic charge powers the NFC tag, causing transmission of information stored in the NFC tag to the remote energy source 11 via an NFC antenna. The data exchange format can be a binary message that is used to encapsulate one or more application-defined payloads having a variety of types and sizes combined into a single message construct described by a type, a length, and an optional identifier. The type, length, and identifier can be used to communicate the device status, e.g., an unpierced film status and a pierced film status.

Figure 12:
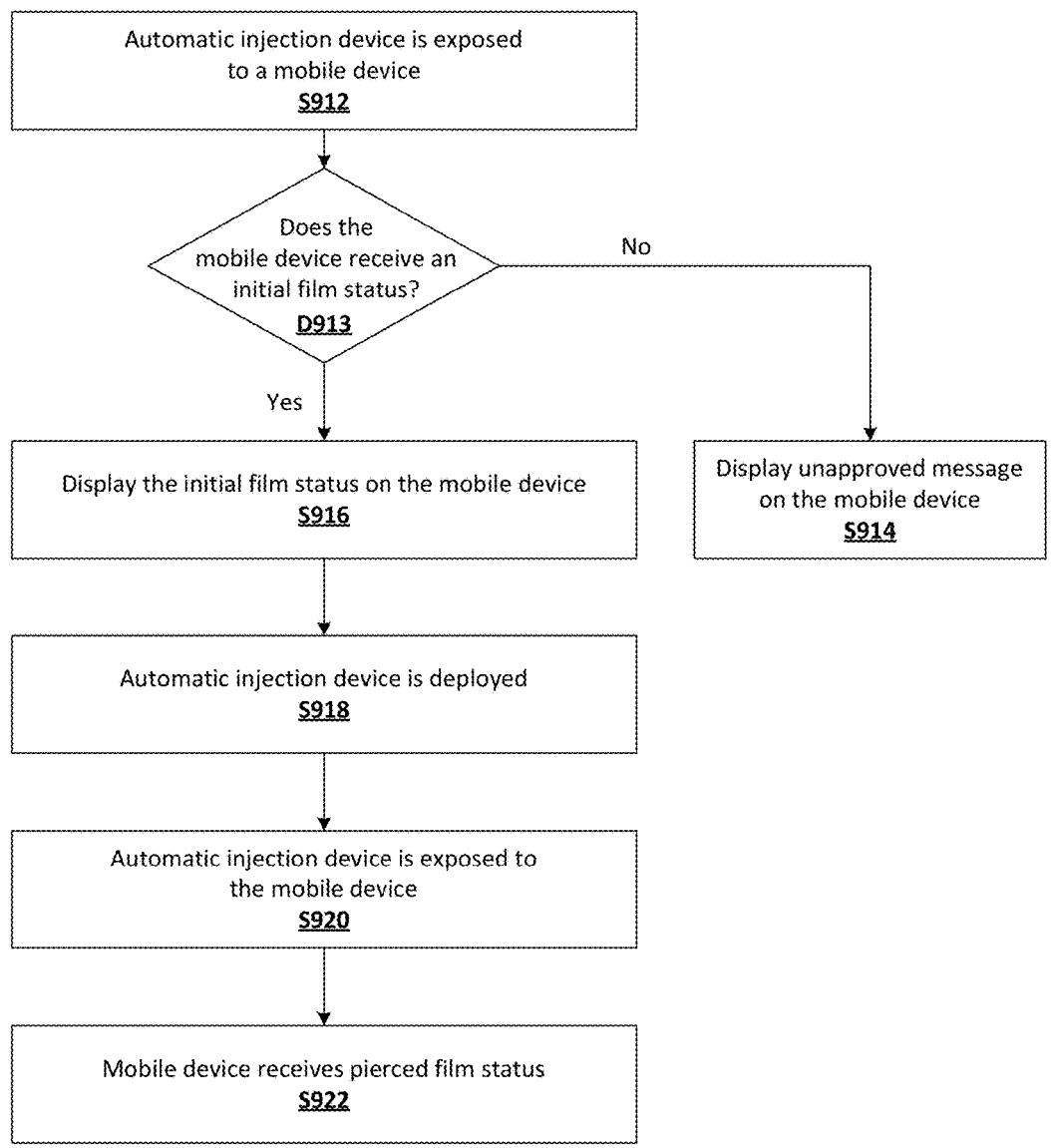
FIG. 12 is a more detailed operational flowchart of a representative embodiment of the method for using the automatic injection device of FIG. 1, according to embodiments of the disclosed subject matter.

With reference now to FIGS. 12-14, a more detailed operational flowchart 901 of a representative embodiment of the disclosed subject matter is provided for illustration and not limitation, according to further aspects of the disclose subject matter. Aspects of operational flowcharts 900 and 901 can incorporate the components, or similar components, to those described above with reference to FIGS. 1-10B. The operational flowchart 901 includes exposing the automatic injection device 10 to the mobile device 11 (S912) to expose the NFC assembly to the remote energy source from the mobile device, and determining whether an initial film status signal is received (D913). If not, an unapproved message is displayed on the mobile device 11 (S914); if an initial film status signal is received, the initial film status is displayed on the mobile device 11 (S916). In this manner, confirmation that the automatic injection device 10 is unused can be obtained. After the initial film status is displayed on the mobile device 10, the automatic injection device 10 can be deployed (S918). The automatic injection device 10 is then exposed to the mobile device 11 again (S920) by the user, such that the mobile device 11 receives a pierced film status (S922). In this manner, confirmation that the contents of the automatic injection device has been delivered can be obtained. Furthermore, a time stamp can be recorded, such as to record the date and time of delivery.

One of several benefits of the disclosed subject matter includes a more efficient automatic injection device and an accurate method for authenticating the device, verifying patient compliance with injection routines by associating the signal generated upon the piercing of the film with patient use of the device and administration of the therapy, and managing injection routines. This can be achieved by integrating (e.g., incorporating) an NFC assembly within the automatic injection device itself, rather than on the automatic injection device's package (e.g., perforated tamper seal packages). For example, an opened package does not necessarily correlate to a used device. Furthermore, the NFC assembly can be passive which does not require a battery for the transmission of data.

Additionally, according to aspects of the disclosed subject matter, real-time monitoring of drug delivery can be achieved with this device and method of using the same. For example, a mobile device can record dates and times when the automatic injection device is used by tracking a device status, depending on the type of device status.

According to further aspects of the disclosed subject matter, the film status can be displayed as a message indicating the medical device is in the initial condition if the unpierced film status is received or that the medical device is in the deployed condition if the pierced film status is received. For example, the message can be displayed on a user's mobile device, or as an indication on the automatic injection device.

Additionally, and as embodied herein, the NFC circuit can include a passive electronic circuit that contains authentication information configured to be machine readable when energized by the remote energy source. The method therefore can further include receiving the authentication information from the NFC circuit and displaying an approved message if the authentication information is recognized or an unapproved message if the authentication information is not recognized.

According to further aspects of the disclosed subject matter, the method further includes creating a time stamp upon confirmation of deployment of the medical device.

According to further aspects of the disclosed subject matter, the film status can be displayed on a user interface, such as the user's mobile device, computer or any other device with a suitable screen. Additionally or alternatively, the film status can be transmitted to a remote server such as a cloud-based server.

Solely for purpose of illustration, reference is now made to FIGS. 15A-16B, in which alternative aspects of the film 832 and film support member 836 are provided, according to aspects of the disclosed subject matter. As embodied herein, the film 832 can be a flexible film having a first film portion 832a disposed on a first side 836a of the film support member 836 and a second film portion 832b disposed on a second side 836b of the film support member 836. Furthermore, the first film portion 832a and the second film portion 832b can be joined via a third film portion 832c which corresponds to a third side 836c of the film support member 836. In this manner, aperture 837 can be covered by the first and second film portions 832a,b on the first and second sides 836a,b, respectively, such that the piercing element 831 pierces both film portions 832a,b when the activation button 32 is moved from the initial position to the actuated position. Additionally, and as embodied herein, the film 832 and film support member 836 may be snap-fit into the activation button 32.

By providing a flexible film, the capacity can increase without increasing the footprint of the automatic injector. A flexible film can fold into multiple layers achieving a smaller footprint, which helps integrate the flexible film into mechanisms. For example, and as embodied herein, the overall dimensions of the NFC assembly can have an outer diameter of about 13 mm and an inner diameter of about 5 mm. Before the first and second portions 832a,b are folded, as embodied herein, the first and second portions 832a,b have a center-to-center distance of about 15.4 mm. Additionally, and as embodied herein, the third film portion can have a width of about 3.5 mm (e.g., equal to about a thickness of the film support member 836).

It is recognized that the device and method of the disclosed subject matter can be used for a variety of autoinjector configurations. For example, and for purpose of illustration and not limitation, reference is now made to FIGS. 17-19, in which an alternative aspect of the firing mechanism assembly 122 is illustrated, according to aspects of the disclosed subject matter. As illustrated, the activation button 32 can be configured as a side activation button such that the piercing element 831 can be configured to project outward from the axis of the tubular firing body 12, with the NFC assembly disposed on the activation button 32 in a similar manner as described above. One skilled in the art will appreciate the many alternative configurations encompassed by the disclosed subject matter and the descriptions and illustrations herein are meant for descriptive purposes and not limitation.

While the disclosed subject matter is described herein in terms of certain preferred embodiments, those skilled in the art will recognize that various modifications and improvements can be made to the disclosed subject matter without departing from the scope thereof. Additional features known in the art likewise can be incorporated, such as U.S. Pub. No. 2014/0207073 and U.S. Pat. No. 8,679,061, each of which is incorporated by reference in its entirety herein. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. A firing mechanism assembly comprising:
a firing body and an activation button moveable relative to the firing body between an initial position and an actuated position, the activation button configured to deploy a plunger when moved to the actuated position, the firing mechanism assembly further including a piercing element extending from at least one of the firing body and the activation button; and
a near-field communication (NFC) assembly comprising a film disposed proximate the piercing element and configured to be pierced by the piercing element upon movement of the activation button to the actuated position, and an NFC circuit configured to indicate a film status including at least an unpierced film status before the film is pierced and a pierced film status after the film is pierced.

2. The firing mechanism assembly of claim 1, wherein the piercing element extends from the firing body and at least a portion of the NFC assembly is carried by the activation button.

3. The firing mechanism assembly of claim 2, wherein the activation button has an aperture defined therein to receive the piercing element when the activation button is moved to the actuated position, the film being aligned with the aperture to be pierced by the piercing element when the activation button is moved to the actuated position.

4. The firing mechanism assembly of claim 3, wherein the NFC assembly includes a film support member with the film mounted thereon, the film support member having an aperture defined therein in alignment with the aperture of the activation button so as to receive the piercing element at least partially therein when the activation button is moved to the actuated position.

5. The firing mechanism assembly of claim 4, wherein the film is attached to the film support member using adhesive bonding, in-mold labelling, or laser welding.

6. The firing mechanism assembly of claim 4, wherein the film is a flexible film and includes a first film portion disposed on a first side of the film support member and a second film portion disposed on a second side of the film support member.

7. The firing mechanism assembly of claim 4, further comprising an activation button cap to secure the film support member on the activation button.

8. The firing mechanism assembly of claim 1, wherein the NFC circuit is disposed on the film.

9. The firing mechanism assembly of claim 1, wherein at least a portion of the NFC circuit is configured to be disabled when the film is pierced by the piercing element to indicate the pierced film status, the pierced film status corresponding to the firing mechanism assembly being unacceptable for use.

10. The firing mechanism assembly of claim 9, wherein the NFC circuit includes a passive electronic circuit that contains authentication information configured to be machine readable when energized by an external energy source.

11. The firing mechanism assembly of claim 10, wherein the NFC circuit includes a first circuit configured to be disabled when the activation button is moved to the actuated position and a second circuit configured to contain the authentication information.

12. An automatic injection device comprising:
a syringe disposed within a syringe housing assembly and configured to be deployed from an initial condition to a deployed condition;
a firing mechanism assembly coupled with the syringe housing assembly and configured when actuated to deploy the syringe from the initial condition to the deployed condition, the firing mechanism assembly including a piercing element; and
a near-field communication (NFC) assembly comprising a film disposed proximate the piercing element and configured to be pierced by the piercing element upon actuation of the firing mechanism assembly, and an NFC circuit configured to indicate a film status including at least an unpierced film status before the film is pierced and a pierced film status after the film is pierced.

13. The automatic injection device of claim 12, wherein at least a portion of the NFC circuit is configured to be disabled when the film is pierced by the piercing element to indicate the pierced film status, the pierced film status indicating the automatic injection device is unacceptable for use.

14. The automatic injection device of claim 13, wherein the NFC circuit includes a passive electronic circuit that contains authentication information configured to be machine readable when energized by an external energy source.

15. The automatic injection device of claim 14, wherein the NFC circuit includes a first circuit configured to be disabled when the firing mechanism assembly is actuated and a second circuit configured to remain enabled when the film is pierced by the piercing element, the authentication information being contained on the second circuit.

16. The automatic injection device of claim 12, wherein the syringe comprises a reservoir having a therapeutic agent disposed therein.

17. A method of using a medical device comprising:
exposing the medical device to a remote energy source, the medical device including a firing mechanism assembly configured when actuated to deploy the medical device from an initial condition to a deployed condition, the firing mechanism assembly including a piercing element and a near-field communication (NFC) assembly comprising a film disposed proximate the piercing element and configured to be pierced by the piercing element upon actuation of the firing mechanism assembly, and an NFC circuit configured, when energized by the remote energy source, to indicate a film status including at least an unpierced film status before the film is pierced and a pierced film status after the film is pierced;

receiving a signal generated from the NFC assembly indicating whether the film status is the pierced film status or the unpierced film status; and displaying the film status based upon the signal received from the NFC assembly.

18. The method of claim 17, wherein the film status is displayed as a message indicating the medical device is in the initial condition if the unpierced film status is received or that the medical device is in the deployed condition if the pierced film status is received.

19. The method of claim 17, wherein the NFC circuit includes a passive electronic circuit that contains authentication information configured to be machine readable when energized by the remote energy source, the method further comprising:

receiving the authentication information from the NFC circuit; and displaying an approved message if the authentication information is recognized or an unapproved message if the authentication information is not recognized.

20. The method of claim 17, further comprising creating a time stamp upon confirmation of deployment of the medical device.

21. The method of claim 17, wherein displaying the film status is performed on a user interface.

22. The method of claim 17, wherein displaying the film status comprises transmitting the film status to a remote server.

* * * * *

UNITED STATES PATENT AND TRADEMARK OFFICE
CERTIFICATE OF CORRECTION

PATENT NO. : 10,300,200 B2  
APPLICATION NO. : 15/906371  
DATED : May 28, 2019  
INVENTOR(S) : James Hughes et al.

Page 1 of 1

It is certified that error appears in the above-identified patent and that said Letters Patent is hereby corrected as shown below:

On the Title Page

In the Abstract, in Column 2, Line 1, delete "A automatic" and insert --An automatic--

Signed and Sealed this  
Seventeenth Day of March, 2020

Andrei Iancu  
*Director of the United States Patent and Trademark Office*